United States Patent
Schnell

[11] Patent Number: 6,090,066
[45] Date of Patent: Jul. 18, 2000

[54] INJECTION SITE WITH OUTER FLANGE

[75] Inventor: William J. Schnell, Libertyville, Ill.

[73] Assignee: DSU Medical Corporation, Las Vegas, Nev.

[21] Appl. No.: 09/126,265

[22] Filed: Jul. 30, 1998

[51] Int. Cl.[7] .................................................. A61M 57/00
[52] U.S. Cl. ............................ 604/86; 604/256; 604/905
[58] Field of Search .................................. 604/86, 88, 93, 604/905, 523, 256

[56] References Cited

U.S. PATENT DOCUMENTS

| | | | |
|---|---|---|---|
| 3,990,445 | 11/1976 | Lundquist | .................................. 604/86 |
| 4,043,333 | 8/1977 | Munsch . | |
| 4,432,767 | 2/1984 | Lobdell et al. | ............................. 604/86 |
| 4,966,582 | 10/1990 | Sit et al. | ..................................... 604/86 |
| 5,069,666 | 12/1991 | Gericke | ....................................... 604/86 |
| 5,071,412 | 12/1991 | Utterberg | ............................. 604/411 X |
| 5,360,407 | 11/1994 | Leonard | ................................. 604/93 X |

*Primary Examiner*—John D. Yasko
*Attorney, Agent, or Firm*—George H. Gerstman; Garrettson Ellis

[57] ABSTRACT

An injection site for passing a needle into an enclosed space surrounded by a wall, typically defined by a tubular section incorporated in a tubular set. An aperture in the wall communicates between the enclosed space and the exterior, having an elastic, needle-pierceable member such as a plug occluding the aperture. The plug is exposed to the exterior on one side and defines a route of needle access through the plug and aperture to the enclosed space. A first flange is positioned adjacent to the plug and extends transversely outwardly from the plug. The first flange carries a second flange, which extends longitudinally relative to the plug, and is spaced transversely outwardly from the plug to define a catch area for needles, which catch area surrounds the plug.

12 Claims, 2 Drawing Sheets

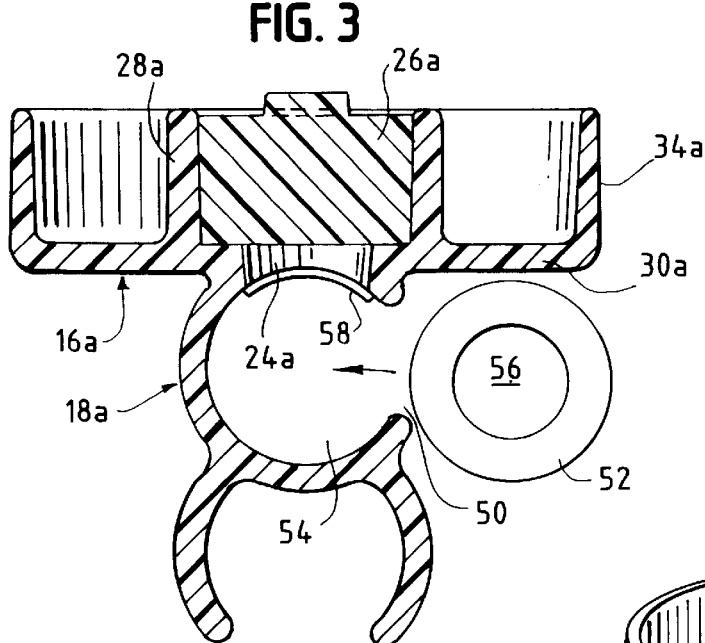
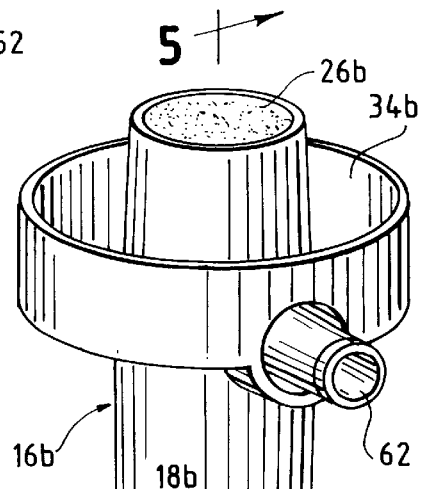
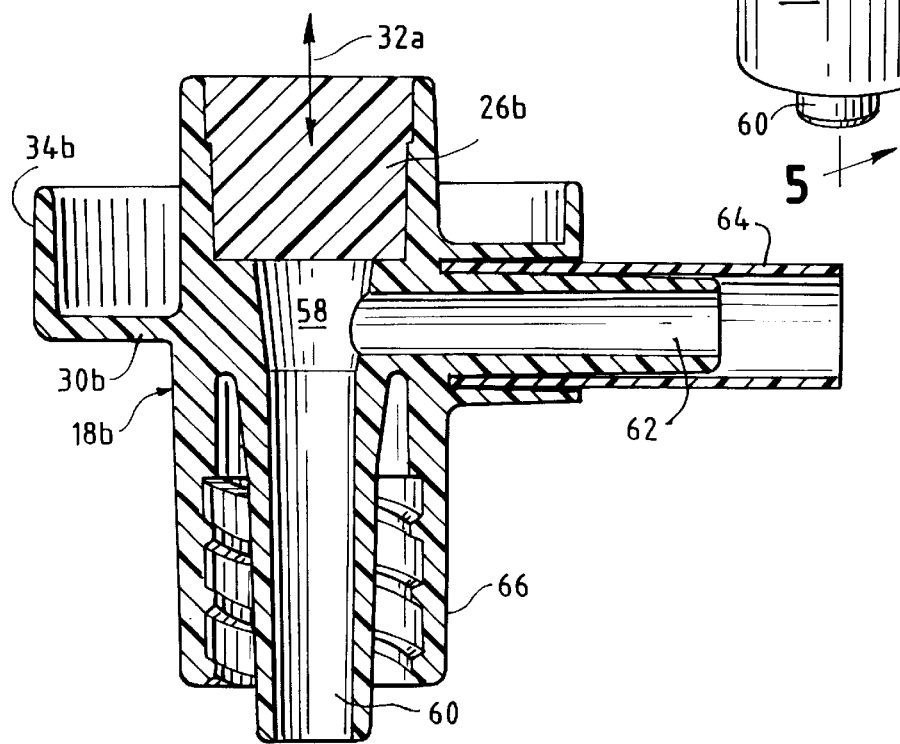

INJECTION SITE WITH OUTER FLANGE

BACKGROUND OF THE INVENTION

Injection sites are used on numerous sets for external medical fluid handling, for example sets for dialysis, blood banking, and IV therapy. Typically, injection sites comprise an aperture which communicates with the flow lumen of tubing through which the medical fluid, blood or solution, passes. A plug of elastomeric material such as natural rubber latex occupies the port, providing a resealable barrier which is penetrable by needles to gain access to the internal flow path of the set.

Many designs of this type of injection site are known. The oldest have no guard, creating the risk that the user can injure him or herself with an errant needle. During the last decade or so, injection sites have incorporated stab guards, which are typically flat or curved shields, beneath which the injection site housing may be grasped by thumb and forefinger. The intent of such a shield is to protect the fingers from a needle which fails to penetrate the elastomeric plug.

However, such shields have not provided adequate protection of the fingers or the hand. A needle may strike the shield at an angle and slide in an involuntary manner outwardly across the periphery of the shield and into the hand. Also, if needles miss the injection site at an angle due to an inattentive user, they can miss the shield entirely.

By this invention, further protection against needle injury is provided to an injection site design. Particularly, a skidding, angled needle can be stopped before it passes across the periphery of the shield used in this invention, thus avoiding injury to the hand in many circumstances where prior art shields would allow such injury.

DESCRIPTION OF THE INVENTION

In accordance with this invention, an injection site is provided for passing a needle into an enclosed space surrounded by a wall. Typically, the enclosed space is the lumen of a tubular structure that fits into sealed engagement with other, flexible tubular sections of a medical blood or solution set. However, the injection site may be used in conjunction with chambers or other devices if desired.

An aperture is defined in the wall, communicating between the enclosed space and the exterior. An elastic, needle-pierceable plug occludes the aperture to prevent a needle from passing through the aperture without passing through the plug. Also, the plug is exposed to the exterior on at least one side, so as to define a route of needle access through the plug and the aperture to the enclosed space.

By this invention, a first flange is positioned adjacent to the plug, the flange extending transversely outwardly from the route of needle access. The first flange carries a second flange, which extends longitudinally relative to the route of needle access, and is spaced transversely outwardly from the plug, to define a catch area for needles surrounding the plug. Preferably, the first flange, the second flange, and the catch area are all annular.

Thus, as a user attempts to pass a needle through the plug of the injection site and misses, for one reason or another, the needle may encounter typically the first flange and skid outwardly until it enters into engagement with the second flange, where the needle motion is stopped, being typically retained at the junction between the first and the second flange. Alternatively, a needle, through in attention, may be advanced at such an angle that it misses the needle-pierceable plug and the first flange, and strikes the second flange first. Then it tends to slide toward the first flange, where it is also captured, ceasing its movement at the junction between the first and second flanges. Thus, in both circumstances the user is protected from a needle stick under circumstances where a conventional, flat- disk injection site shield of similar size would have permitted a needle stick to take place. Typically, the aperture which is occluded by the elastic plug is defined by a tube-defining body. The body may have fittings for receiving a pair of flexible tubes in sealed connection with the body and aperture, so that the body is part of a flow path along a flexible, tubular set for handling of medical fluids.

The body may further define an outwardly projecting handle for manual or mechanical retention of the body as may be desired. This handle may be of any design, but preferably comprises a pair of curved members projecting outwardly from said body in typically convex relation to each other. These curved members may be manually held, but they may also be used to snap fit into a recess on dialysis machines or the like, which carry such a recess permitting retention of the injection site to the machine and its removal therefrom. Also, the convex, curved members may also be used to clip to another tube for retention.

The injection site of this invention may have a route of needle access which is generally transverse to a path of flow for blood or medical solution through the injection site. Alternatively, the route of needle access may be longitudinal or generally parallel to at least some of the path of flow through the injection site. Also, the injection site may be mounted on the end of a tube with the axis of the tube being generally parallel to the route of needle access.

Also, the hollow body of the injection site may have a fitting for a male or female luer connection, which fitting communicates with the enclosed space. Thus the injection site may be attached at any luer connection site.

Likewise, the hollow body may define an opening which is capable of receiving plastic blood or medical solution tubing. Thus, the tubing within the hollow body defines the enclosed spaced described above, with a needle passing through the aperture in the wall and the needle pierceable plug, but also passing through the plastic tubing itself to enter the enclosed space. An appropriate seal may be provided on the hollow body about the area of the plastic blood tubing to prevent leakage of fluids after penetration by a needle.

DESCRIPTION OF THE DRAWINGS

FIG. 3 is a transverse sectional view of another embodiment of an injection site of this invention, which is mountable upon tubing of a medical fluid set from the side, and functions effectively as an injection site wherever it is placed;

FIG. 4 is a perspective view of another embodiment of the injection site of this invention; and FIG. 5 is a longitudinal, sectional view of the injection site of FIG. 4.

DESCRIPTION OF SPECIFIC EMBODIMENTS

Figure 1:
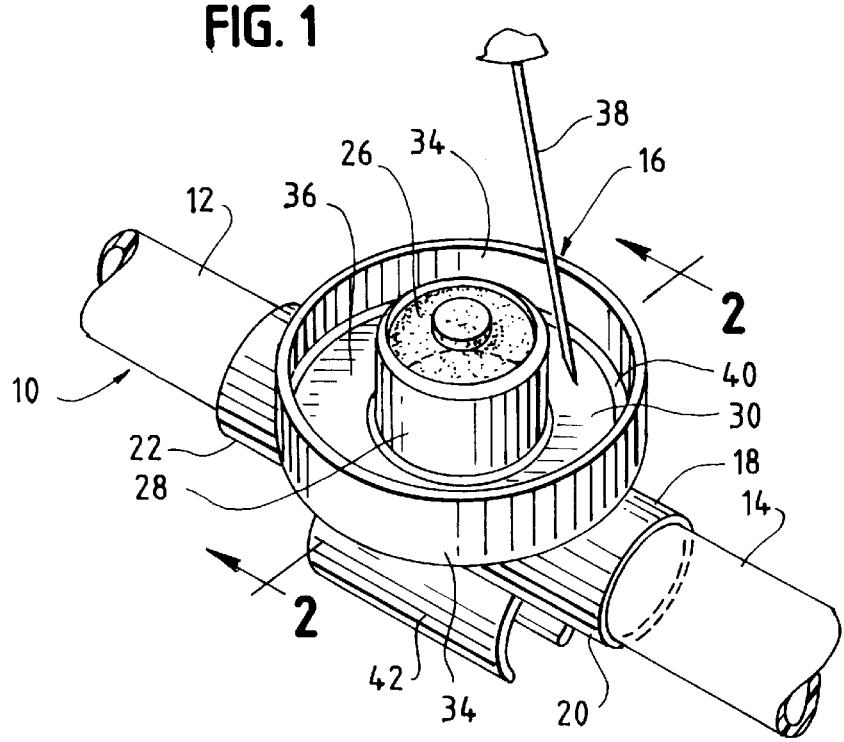
FIG. 1 is a fragmentary, perspective view of a medical fluid set comprising flexible tubing and a first embodiment of the injection site of this invention.
Figure 2:
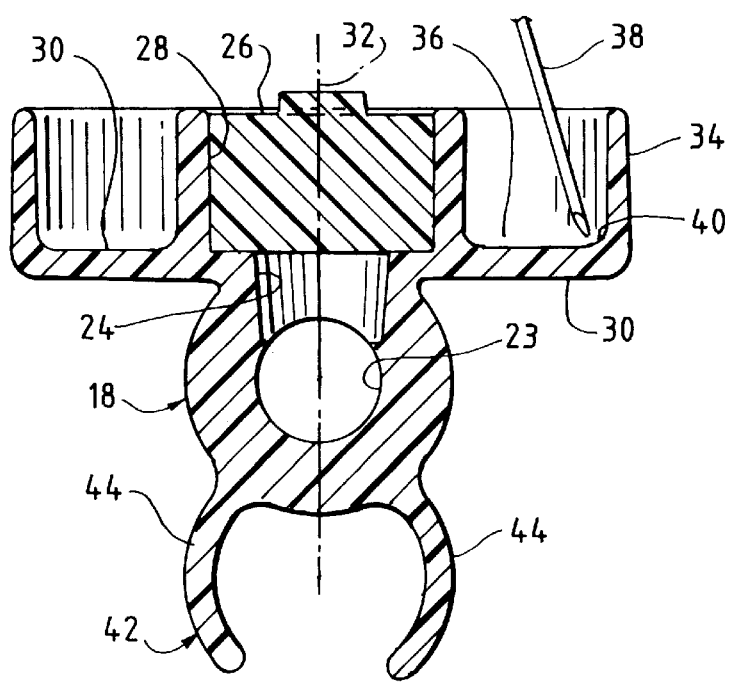
FIG. 2 is a transverse sectional view of the injection site of FIG. 1.

Referring to FIGS. 1 and 2, a portion of an otherwise conventional medical fluid set 10 is disclosed. Set 10 may be of any desired design, comprising lengths of flexible tubing 12, 14 for the flow of blood or other medical solution, the ends of the respective tubing 12, 14 being conventionally sealed within opposed tubular fittings 20, 22 of injection site 16.

Injection site 16 comprises a tube-defining body 18 which, in turn, defines the above-named fittings 20, 22. Body 18 defines a lumen 23 (previously called the "enclosed space") extending therethrough into communication with the respective lumens of tubes 12, 14. An aperture 24 is defined in body 18, to provide communication between lumen 23 and the exterior.

An elastic, needle-pierceable and resealable plug 26 of generally conventional design is retained in a recess defined by annular wall 28, in a position to occlude aperture 24 so that a needle cannot enter aperture 24 or lumen 23 without passing through needle pierceable plug 26. Annular wall 28 and other parts may comprise an integral part of body 18, which may be molded as a single piece, with the parts being shown more particularly in FIG. 2.

In accordance with this invention, first flange 30 is shown to comprise an annular disk which is positioned adjacent to plug 26 and which extends transversely outwardly from the plug and from the general route of needle access as indicated by line 32. The needle penetrates plug 26 to enter into communication with aperture 24 and lumen 23.

By this invention, a second flange 34 is provided, shown to be annular in this embodiment and integral with first flange 30. Second flange 34 forms a cylindrical section in this embodiment, extending longitudinally relative to route of needle axis 32, and spaced transversely outwardly from plug 26 and wall 28, to define an annular catch area 36 surrounding plug 26 and wall 28 for the purpose of catching errant needles. By way of specific example, a needle 38 is shown, which needle has been advanced by an inattentive user toward plug 26, but which has missed the target. In that circumstance, needle 38 enters catch area 36 and impacts the inner wall of either flange 30 or 34. From there, the needle quickly tends to slide toward the annular junction area 40 of walls 30, 34, at which point the motion of the needle tends to stop.

It can be seen that if needle 38 enters the annular catch area 36, it is very unlikely for it to inadvertently slip out again until the user has realized that he or she has missed the target, and purposefully withdraws the needle. Contrary to flat shields of the prior art, an errant needle cannot be accidentally deflected outwardly along first flange 30 to cross the outer periphery of the shield and to stab whatever part of the hand is exposed beyond the shield. Instead, the needle is caught, stopped, and retained until the user realizes the mistake. Thus, accidental needle sticks are greatly reduced, even though the first flange 30 may be no larger than corresponding, flat needle sheath flanges of the prior art.

Injection site 10 also carries a handle 42 which comprises a pair of convex walls 44 connected to body 18 at one end of the walls. These may be used as a manual handle, or they may be used for retention in snap-fit manner with an appropriate retainer member on apparatus such as dialysis apparatus, to help keep the set to which the injection site belongs in an orderly array during use. Also it may clip to tubing.

Referring to FIG. 3, an injection site 16a is disclosed which is similar in structure to the injection site of FIGS. 1 and 2 except as otherwise described herein.

Tube defining body 18a is provided as in the previous embodiment, but, in this embodiment, body 18a defines a lateral opening 50 which is not found in the previous embodiment. Because of the presence of opening 50, it is possible to mount injection site 16a on plastic tubing 52 of a large variety of fluid flow sets simply by forcing plastic tubing 52 into the interior 54 of body 18a, which interior is typically of larger diameter than the corresponding lumen 23 of the previous embodiment, to provide room, but typically with a tight fit, for the tubing 52 and its flow lumen 56.

Aperture 24a then corresponds to aperture 24 of the previous embodiment although it may be filled with a portion 58 of elastic, needle pierceable and resealable plug 26a, which is for the same purpose as plug 26 of the previous embodiment. Portion 58 may provide an added seal against the outer surface of plastic tube 52 when it is emplaced within body 18a.

When a needle is projected through sealing plug 26a, it also passes through the wall of tube 52 to engage flow lumen 56. Section 58 of the plug 26a can provide a surrounding seal of needle punctures in tube 52, permitting a substantial number of different needle sticks extending through plug 26a without substantial leakage.

As in the previous embodiment, first flange 30a and second annular flange 34a are provided in a manner similar to a previous embodiment, (along with annular wall 28a) to catch advancing needles and to protect the user from needle sticks in a manner which is substantially identical to that previously described with respect to the last embodiment.

Thus, this particular embodiment is capable of being mounted wherever desired upon tubing of a blood or solution flow set, to provide needle access to the set at that point plus resealing after withdrawal of the needle.

Turning to FIGS. 4 and 5, a third embodiment of the injection site 16b of this invention is disclosed. In the previous embodiments, the route of needle access 32 was generally transverse to the path of flow of blood or solution through the respective flow lumens 23 or 56. In this present embodiment, the same route of needle access 32a can be generally parallel to at least some of the path of flow through the injection site.

Specifically, tube defining body 18b defines an enclosed space 58 which communicates with a tapered, tubular luer connector 60 which extends in a direction generally parallel to the route of needle access 32a, and forming part of the flow path through the injection site. The other part of the flow path comprises a rigid tube 62 which is positioned transversely of needle access 32a and the longitudinal axis of luer tube 60, with the two tubes 60, 62 communicating with each other through enclosed space 58 to form a flow path.

Injection site 18b may be carried on flexible tubing 64, which can surround rigid, tubular member 62 and be bonded thereto so that injection site 18b is carried on the end of a tubular set. In use, injection site 18b may be attached to a wide variety of luer or luer lock connectors to make desired connections with other ports, sets, and/or containers. Outer skirt 66 may carry a conventional thread for a luer lock system.

Alternatively, one or both of tubes 60, 62 may define or carry a universal connector of the type described in U.S. Pat. No. 5,071,413, so that connection may be made with luer connectors and also through pierceable diaphragms and the like.

In this embodiment of FIGS. 4 and 5, a similar flange 30b and annular flange 34b is provided for the same needle catching function as is previously described, so that users of injection site 18b can press needles through elastomeric, resealable plug 26*b* to gain needle access to enclosed space 58 with increased safety against accidental needle sticks.

Thus, an injection site is provided which may have a protective flange of no greater diameter than the flanges of the prior art, but which provides substantially increased safety to the user against needle sticks.

The above has been offered for illustrative purposes only, and is not intended to limit the scope of the invention of this application, which is as defined in the claims below.

That which is claimed:

1. An injection site used for passing a needle into an enclosed space surrounded by a wall, which comprises:

an aperture in said wall communicating between said enclosed space and the exterior; an elastic, needle pierceable member occluding said aperture and exposed to the exterior to define a route of needle access through said member and aperture to the enclosed space; a first flange positioned adjacent to said member and extending transversely outwardly from said route of needle access, said first flange carrying a second flange extending longitudinally relative to said route of needle access and spaced transversely outwardly from said member to define a catch area for needles surrounding said plug, in which said aperture is defined by a tube-defining body, said body having a pair of tube fittings communicating with said enclosed space and extending in opposed directions substantially perpendicular to said route of needle access for receiving a pair of flexible tubes in sealed connection with said body and aperture.

2. The injection site of claim 1 in which said first flange is planar and substantially perpendicular to the route of needle access, said needle-pierceable member extending outwardly from said first flange and said tube fittings.

3. The injection site of claim 2 in which said first and second flanges are annular, to form an annular catch area.

4. The injection site of claim 1 in which said first and second flanges are annular, to form an annular catch area.

5. The injection site of claim 1 in which said pierceable member is surrounded by a tubular wall, which tubular wall is integral with the first flange and extending parallel to the second flange.

6. An injection site used for passing a needle into an enclosed space surrounded by a wall, which comprises:

an aperture in said wall communicating between said enclosed space in the exterior; an elastic, needle pierceable member occluding said aperture and exposed to the exterior to define a route of needle access through said pierceable member and aperture to the enclosed space; a first flange positioned adjacent to said pierceable member and extending transversely outwardly from said route of needle access, said first flange carrying a second flange extending longitudinally relative to said route of needle access and spaced transversely outwardly from said pierceable member to define a catch area for needles surrounding said pierceable member, said aperture being defined by a hollow body, said body having a fitting for receiving plastic blood or medical solution tubing in a position abutting to said aperture, whereby said tubing within the fitting defines said enclosed space.

7. The injection site of claim 6 in which said first flange is planar and substantially perpendicular to the route of needle access, said needle-pierceable member extending outwardly from said first flange and said tube fitting.

8. The injection site of claim 7 in which said first flange is circular and said second flange is annular, to form an annular catch area.

9. The injection site of claim 8 in which said pierceable member is surrounded by a tubular wall, which tubular wall is integral with the first flange and extending parallel to the second flange.

10. A tubular set which comprises a pair of lengths of flexible tubing, said lengths of tubing being connected in fluid flow relationship to an injection site for passing a needle into an enclosed space of the injection site, said enclosed space communicating with the lumens of said flexible lengths of tubing, said injection site defining a housing and comprising:

an aperture in said housing communicating between the lengths of flexible tubing and the exterior; an elastic, needle pierceable member occluding said aperture and exposed to the exterior to define a route of needle access through said pierceable member and aperture to the enclosed space; a first flange positioned adjacent to said needle-pierceable member and extending transversely outwardly from said route of needle access, said first flange carrying a second flange extending longitudinally relative to said route of needle access and spaced transversely outwardly from said needle-pierceable member, to define a catch area for needles surrounding said plug, said housing having a pair of fittings communicating respectively with said lengths of flexible tubing, said fittings extending in opposed directions substantially perpendicular to said route of needle access, said route of needle access being substantially perpendicular to a path of flow through said lengths of flexible tubing and said housing.

11. The injection site of claim 10 in which said first flange is planar and substantially perpendicular to the route of needle access, said needle-pierceable member extending outwardly from said first flange and said tube fittings.

12. The tubular set of claim 11 in which said first flange is circular and said second flange is annular, forming an annular catch area.

\* \* \* \* \*